(12) United States Patent
Potyrailo et al.

(10) Patent No.: US 10,551,338 B2
(45) Date of Patent: Feb. 4, 2020

(54) SYSTEMS AND METHODS FOR SENSING COMPOUNDS IN AN ENVIRONMENT

(71) Applicant: GENERAL ELECTRIC COMPANY, Schenectady, NY (US)

(72) Inventors: Radislav Alexandrovich Potyrailo, Niskayuna, NY (US); Zhexiong Tang, Niskayuna, NY (US); Igor Tokarev, Waterford, NY (US); Binil Itty Ipe Kandapallil, Summerville, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 332 days.

(21) Appl. No.: 15/280,028

(22) Filed: Sep. 29, 2016

(65) Prior Publication Data

US 2018/0088064 A1    Mar. 29, 2018

(51) Int. Cl.
*G01N 27/22* (2006.01)

(52) U.S. Cl.
CPC ................... *G01N 27/221* (2013.01)

(58) Field of Classification Search
CPC ............................ G01N 27/02; G01N 27/221
See application file for complete search history.

(56) References Cited

U.S. PATENT DOCUMENTS

| | | | |
|---|---|---|---|
| 5,756,879 A | 5/1998 | Yamagishi et al. | |
| 6,500,547 B1 | 12/2002 | Potyrailo | |
| 9,052,263 B2 | 6/2015 | Potyrailo | |
| 2013/0313111 A1* | 11/2013 | Nishida | G01N 27/02 204/415 |
| 2014/0011286 A1 | 1/2014 | Potyrailo et al. | |
| 2015/0293057 A1 | 10/2015 | Mohanty et al. | |

OTHER PUBLICATIONS

Amin, Emran Md, Jhantu Kumar Saha, and Nemai Chandra Karmakar. "Smart sensing materials for low-cost chipless RFID sensor." IEEE Sens. J 14.7 (2014): 2198-2207.*
Javed, Nimra, et al. "Directly printable moisture sensor tag for intelligent packaging." IEEE Sensors Journal 16.16 (2016): 6147-6148.*
Ong, K. G., et al. "Monitoring of bacteria growth using a wireless, remote query resonant-circuit sensor: application to environmental sensing." Biosensors and Bioelectronics 16.4-5 (2001): 305-312.*
Kauffman, et al., "Carbon Nanotube Gas and Vapor Sensors.", Angew Chem Int Ed Engl., vol. 47, Issue: 35, pp. 6550-6570, 2008.

(Continued)

*Primary Examiner* — Robert J Eom
(74) *Attorney, Agent, or Firm* — Fletcher Yoder, P.C.

(57) ABSTRACT

The subject matter of the present disclosure generally relates to systems and methods for sensing analytes with a high selectivity and low responses to interferences in an environment. In one embodiment, a sensor was developed which comprises a sensor electrode, a coupling element operationally coupled to a discrete segment of the sensor electrode, and an activation material in operational contact with the coupling element and configured to induce an irreversible sensor response for a selected sensing application.

27 Claims, 10 Drawing Sheets

(56) References Cited

OTHER PUBLICATIONS

Jurs, et al., "Computational Methods for the Analysis of Chemical Sensor Array Data from Volatile Analytes", Chem. Rev., vol. 100, Issue: 7, pp. 2649-2678, Jun. 7, 2000.

Hatchett, et al., "Composites of Intrinsically Conducting Polymers as Sensing Nanomaterials", Chem. Rev., vol. 108, Issue: 2, pp. 746-769, Jan. 3, 2008.

Rock, et al., "Electronic Nose: current Status and future Trends" Chem. Rev 2008, vol. 108, pp. 705-725.

Azzarelli, et al., "Wireless Gas Detection With a Smartphone via RF Communication", PNAS, Dec. 23, 2014, vol. 111, No. 51, pp. 18162-18166.

Zhu, et al., "Wireless Hazard Badges to Detect Nerve-Agent Simulants", Angew Chem Int Ed, 2016, vol. 55, pp. 1-6.

Joo, et al., "Chemical Sensors with Integrated Electronics", Chem Rev 2008, vol. 108, pp. 638-651.

\* cited by examiner

SYSTEMS AND METHODS FOR SENSING COMPOUNDS IN AN ENVIRONMENT

STATEMENT OF GOVERNMENT SUPPORT

This invention was made with government support under the grant number NAVY-13-C-3014 awarded by Department of Defense. The government has certain rights in the invention.

TECHNICAL FIELD

Embodiments of the present invention relate generally to systems and methods for sensing compounds or analytes in an environment, and more particularly to systems and methods for sensing volatile and non-volatile analytes with high analyte selectivity and low sensor response to interferences in the environment.

BACKGROUND

A known problem in the field of sensing is cross-sensitivity of a sensor, that is, the sensor's undesirable responses to interferences such as compounds other than an analyte to be detected, or physical environmental factors including but not limited to temperature, humidity, and pressure. Cross-sensitivity of the sensor is particularly problematic when the analyte to be detected is at a very low concentration such as a trace level, and a strong response of the sensor to interferences masks the response of the sensor to the analyte. For example, a high level sensor response to humidity may interfere with a response of the sensor built to detect a trace level of explosives.

The problem of cross-sensitivity is typically addressed by arranging a plurality of sensors into a sensor array and processing the array responses using multivariate analysis. In the sensor array, individual sensors are coated with different sensing materials and one response per sensing material (e.g., resistance, current, capacitance, work function, mass, optical thickness, light intensity) is measured. However, the sensor array approach increases numbers of sensors used, and introduces complexity of sensing material deposition and device fabrication.

Using a sensor array instead of a single sensor allows sensor responses to be corrected for interferences such as humidity and typically works over a short period of time. However, independent drift of each sensor in the sensor array may occur over long term, making it necessary to perform frequent calibrations of sensors, which are often labor intensive and time consuming.

The independent drift of each sensor in the sensor array is a result of using different sensing material for each sensor in an array. Each sensor would have its own drift and degradation profile, uncorrelated with the profiles of other sensors. This uncorrelated drift of each sensor leads to significant challenges in keeping sensor arrays within their original specifications.

Another known challenge in sensing is detection of non-volatile compounds in an environment, such as particulates of different natures. Non-limiting examples of such particulates include inorganic particles such as oxidizer salts, organic particles such as explosives, and biological particles such as viruses and spores. At present, detection of particles in an environment (for example, air) often requires complicated equipment including, for example, a pump for air sampling, a set of filters, baffles, or other engineered structures to separate only particles of interest from the rest of collected debris, and a detector to analyze the particles of interest.

Therefore, there is an ongoing need for an improved system and method for sensing volatile and non-volatile analytes in an environment by using a single sensor having high analyte selectivity, low response to interferences, and minimized needs for frequent calibrations. In addition, there is a continuing need for rapid sensing techniques especially for certain sensing applications including but not limited to security applications, for example, detection of explosives in airports and the like.

BRIEF DESCRIPTION

The embodiments disclosed in the present invention provide systems and associated methods for sensing compounds or analytes in an environment with high analyte selectivity, low response to interferences, and minimized needs for frequent calibrations. However, the embodiments disclosed in the present invention should not be limited to solve only the problems stated in this application, but may solve other problems in other areas.

The invention includes, but is not limited to, the following embodiments:

One embodiment includes a sensor comprising: a sensor electrode; a conducting element operationally coupled to a discrete segment of the sensor electrode; and an activation material in operational contact with the conducting element and configured to induce an irreversible sensor response for a selected sensing application.

Another embodiment includes a method for sensing an analyte in an environment, the method comprising the steps of: configuring a sensor for sensing the analyte in the environment, the sensor comprising: a sensor electrode; a conducting element operationally coupled to a discrete segment of the sensor electrode; and an activation material in operational contact with the conducting element and configured to induce an irreversible sensor response for a selected sensing application; allowing the activation material to interact with the analyte; inducing the irreversible sensor response for a selected sensing application; and detecting the irreversible sensor response.

Yet another embodiment includes a system for sensing an analyte in an environment, the system comprising: a sensor comprising: a sensor electrode; a conducting element operationally coupled to a discrete segment of the sensor electrode; and an activation material in operational contact with the conducting element and configured to induce an irreversible sensor response for a selected sensing application; a reader communicatively coupled to the sensor to obtain information from the sensor; and a communication unit configured to provide an infrastructure for communication of the sensor with the reader.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1A:
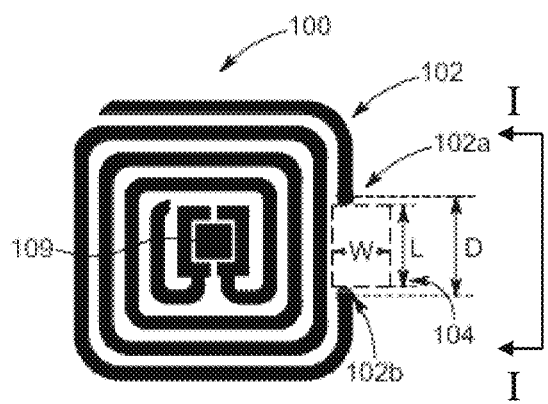
FIG. 1A is a schematic representation of a sensor according to an embodiment.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to, "for example", "for instance", "such as", "e.g.", "including", "include", "in certain embodiments", "and the like", and "in one (an) embodiment".

The term "coupled" as used herein is intended to signify that distinct elements are joined, linked or otherwise connected together directly or indirectly.

The term "writer/reader" includes, but is not limited to, a combination of devices to write and read data into a memory of a memory chip.

The term "in operational contact" as used herein is intended to signify that the operational contact may be achieved by direct contact or through a gap or space.

Traditionally, to coat a sensor with a sensing material or film, the sensing material is applied onto either the whole area or a portion of a sensor electrode of the sensor and the sensing material forms a sensing region. The properties of the sensing region (for example, conductivity) may be reversibly affected upon interaction with an analyte and/or interferences. The final sensor response is a result of combined contributions from both the analyte and interferences. Accordingly, when the sensor is exposed to an environment that contains an analyte and interferences, the signal from the sensing region is affected by both the analyte and interferences, resulting in a low analyte selectivity. This is especially problematic when strong responses from interferences mask a significantly weaker response from the analyte when the concentration of analyte is very low, for example, at a trace level. Added to the challenge is that the effect of analyte on the properties of the sensing region and corresponding sensor response is generally predictable while the effect of interferences on the sensor response is generally unpredictable. As such the unpredictable sensor response contribution from interferences makes it difficult to separate out the influence from the interferences from the total sensor response.

In contrast, the current invention discloses systems and methods for sensing analytes with a high analyte selectivity and low responses to interferences in an environment. This is achieved by utilizing a sensor comprising a sensor electrode, a coupling element operationally coupled to a discrete segment of the sensor electrode, and an activation material in operational contact with the coupling element (for example, disposed on a surface of the conducting element). The interaction between the activation material and an analyte promotes or affects an irreversible change of the conducting element. The irreversible change of the conducting element further induces irreversible sensor response for selected sensing applications. The irreversible change may be a permanent change that cannot be reversed under the operating conditions of the sensor. By comparison, any potential interactions between the activation material and interferences do not lead to an irreversible change of the conducting element and irreversible sensor response. Because the irreversible sensor response is mainly induced by the analyte and not the interferences, a higher analyte selectivity and lower response to interferences can be achieved in detecting and monitoring analytes in an environment for selected sensing applications.

More specifically, in certain embodiments, the activation material interacts with the analyte to form an interaction product that promotes the irreversible change of the conducting element (for example, the interaction product may irreversibly oxidize the conducting element). The irreversibly changed conducting element has one or more different properties compared to the unchanged conducting element, and produces a stronger, irreversible sensor signal (for example, the irreversibly oxidized conducting element may have a lower conductivity and significantly increased sensor resistance response than the unchanged or un-oxidized conducting element). By comparison, no interaction product is formed between the activation material and interferences. As such no irreversible change to the conducting element occurs, and the sensor response does not change in presence of interferences. Because the sensor response is irreversibly changed (for example, increased) in the presence of the analyte and not in the presence of interferences, a higher analyte selectivity can be achieved.

Furthermore, the conducting element constitutes a sensing region and typically is relatively smaller compared to the sensor electrode, and can be easily configured. For example, the thickness of the conducting element may be configured to be of much smaller thickness than the sensor electrode (for example, the thickness of the conducting element may be in a range from about 100 nanometers to about 1000 nanometers, or about 20-1000 fold thinner than the rest of the sensor electrode). The relatively thinner, smaller conducting element ensures that a complete irreversible change of the conducting element can occur across the entire relatively smaller sensing region, thus maximizing the impact of the irreversible change of the conducting element on the high analyte selectivity.

The conducting element may be provided as a single use or disposable unit and may be disposed of after each use.

Numerous previously published results disclosed sensor structures with a small sensing region where a portion of the sensor electrode was cut and replaced with a sensing film. The sensors of the current design provide significant improvements and advantages over other reported sensors, for example, sensors of the current design provide selective responses to analytes over interferences. This selectivity feature is achieved by the unique sensor structure comprising an activation material and a conducting element.

The disclosed technical solution offers several additional advantages, for example, the sensor design is versatile and can be easily configured for selected sensing applications to detect various analytes including gaseous compounds and particulates in an environment. In addition, by using only one sensor, the disclosed system offers simplified material deposition and device fabrication, and decreased data analysis and data processing noise. Also, the sensing region is reduced to only a small region of the sensor structure, thereby reducing the manufacturing cost.

It is to be appreciated that the invention described herein may be used in various applications. By way of examples, measuring the presence of analytes by discerning a change in certain environmental variables within or surrounding a sensor may be useful in monitoring changes in biopharmaceutical products for degradation, monitoring industrial areas for chemical or physical hazards such as toxic gases and vapors, security applications such as residential home monitoring or homeland security in airports (e.g., detection of explosives, vapors leaking from cargo containers in transit), detection of food or beverage spoilage (e.g., vapors evolving during food storage), detection of volatile organic compounds (VOCs) (e.g., volatile organic chemicals, toxic gases, or vapors evolving during storage of chemicals), detection of feces or flatulence (i.e., personal care monitoring), occupational exposure monitoring, air or water monitoring, and other public venues wherein detection of certain harmful substances and/or toxic vapors may be particularly useful.

The advantages of the versatile sensor design disclosed herein can be achieved by using combinations of conducting elements and activation materials for certain analytes of interests. Table 1 shows non-limiting examples of analytes and combinations of conducting elements/activation materials used for various sensing applications.

TABLE 1

Examples of analytes and sensor materials for selected sensing applications.

| Analyte | Conducting element | Activation material | Sensing Application |
|---|---|---|---|
| Chlorate salts | Silver | Polystyrene sulfonic acid | Detection of explosive oxidizers |
| Chlorite salts | Silver | Polystyrene sulfonic acid | Detection of salt residues after disinfection treatment |
| Nitrate salts | Copper | Solvent | Detection of explosive oxidizers & fertilizer residues in vegetables/fruits |
| Inorganic acids | Copper | Solvent | Monitoring of corrosive substances in the ambient environment, e.g., sulfuric & nitric acids in acid rain |
| Organic acids | Copper | Solvent | Detection of fungi & mold |
| TATP | Silver | Polystyrene sulfonic acid | Detection of peroxide based explosives |

The versatile sensor design also allows detection of both volatile and non-volatile analytes in the environment. Non-limiting examples of various analytes are presented in Tables 2-4 below. Table 2 shows non-limiting analyte examples of chemical agents.

TABLE 2

Examples of categories of chemical agents

| Nerve Agents | Blister (Vesicant) Agents | Pulmonary (Choking) Agents | Blood Agents |
|---|---|---|---|
| GA—Tabun | HD—Sulfur Mustard | CG—Phosgene | CK—Cyanogen chloride |
| GB—Sarin | HN—Nitrogen Mustard | DP—Diphosgene | AC—Hydrogen cyanide |
| GD—Soman | L—Lewisite | Cl—Chlorine | SA—Arsine |
| GF—Cyclosarin | MD—Methyl-dichloroarsine | PS—Chloropicrin | KCN—Potassium cyanide |
| VX—Methyl-phosphonothioic Acid | PD—Phenyl-dichloroarsine | DM—Adamsite | NaCN—Sodium cyanide |
| Novichok | ED—Ethyl-dichloroarsine | BCME—Bis(chloro-methyl) ether | |
| | | $NH_3$—Anhydrous ammonia | |

Table 3 shows non-limiting analyte examples of toxic industrial materials listed by Hazard Index.

TABLE 3

Examples of toxic industrial materials listed by Hazard Index.

| High | Medium | Low |
|---|---|---|
| Ammonia | Acetone cyanohydrin | Allyl isothiocyanate |
| Arsine | Acrolein | Arsenic trichloride |
| Boron trichloride | Acrylonitrile | Bromine |
| Boron trifluoride | Allyl alcohol | Bromine chloride |
| Carbon disulfide | Allylamine | Bromine pentafluoride |
| Chlorine | Allyl chlorocarbonate | Bromine trifluoride |
| Diborane | Boron tribromide | Carbonyl fluoride |
| Ethylene oxide | Carbon monoxide | Chlorine pentafluoride |
| Fluorine | Carbonyl sulfide | Chlorine trifluoride |
| Formaldehyde | Chloroacetone | Chloroacetaldehyde |
| Hydrogen bromide | Chloroacetonitrile | Chloroacetyl chloride |
| Hydrogen chloride | Chlorosulfonic acid | Crotonaldehyde |
| Hydrogen cyanide | Diketene | Cyanogen chloride |
| Hydrogen fluoride | 1,2-Dimethylhydrazine | Dimethyl sulfate |
| Hydrogen sulfide | Ethylene dibromide | Diphenylmethane-4,4'-diisocyanate |
| Nitric acid, fuming | Hydrogen selenide | Ethyl chloroformate |
| Phosgene | Methanesulfonyl chloride | Ethyl chlorothioformate |
| Phosphorus trichloride | Methyl bromide | Ethyl phosphonothioic dichloride |
| Sulfur dioxide | Methyl chloroformate | |

TABLE 3-continued

Examples of toxic industrial materials listed by Hazard Index.

| High | Medium | Low |
|---|---|---|
| Sulfuric acid | Methyl chlorosilane | Ethyl phosphonic dichloride |
| Tungsten hexafluoride | Methyl hydrazine | |
| | Methyl isocyanate | Ethyleneimine |
| | Methyl mercaptan | Hexachlorocyclopentadiene |
| | Nitrogen dioxide | Hydrogen iodide |
| | Phosphine | Iron pentacarbonyl |
| | Phosphorus oxychloride | Isobutyl chloroformate |
| | | Isopropyl chloroformate |
| | Phosphorus pentafluoride | Isopropyl isocyanate |
| | | n-Butyl chloroformate |
| | Selenium hexafluoride | n-Butyl isocyanate |
| | Silicon tetrafluoride | Nitric oxide |
| | Stibine | n-Propyl chloroformate |
| | Sulfur trioxide | Parathion |
| | Sulfuryl chloride | Perchloromethyl mercaptan |
| | Sulfuryl fluoride | sec-Butyl chloroformate |
| | Tellurium hexafluoride | tert-Butyl isocyanate |
| | n-Octyl mercaptan | Tetraethyl lead |
| | Titanium tetrachloride | Tetraethyl pyrophosphate |
| | Trichloroacetyl chloride | Tetramethyl lead |
| | Trifluoroacetyl chloride | Toluene 2,4-diisocyanate |
| | | Toluene 2,6-diisocyanate |

Table 4 shows non-limiting analyte examples of explosives, taggants, and oxidizers.

TABLE 4

Examples of explosives, taggants, and oxidizers.

Low Explosives

Black powder
Black powder substitute
Smokeless powder

High Explosives 2,4,6-trinitrotoluene (TNT)
Triacetone triperoxide (TATP)
Pentaerythritol tetranitrate (PETN)
Cyclotrimethylene trinitramine or RDX
Cyclotetramethylene tetranitramine or HMX Taggants 2,3-dimethyl-2,3-dinitrobutane (DMNB)
Ethylene glycol dinitrate (EGDN)
ortho-mononitrotoluene (o-MNT)
para-mononitrotoluene (p-MNT)

Oxidizers

Ammonium nitrate
Urea nitrate
Potassium chlorate
Sodium chlorate
Potassium perchlorate
Potassium nitrate
Ammonium perchlorate
Potassium permanganate FIG. 1A shows a schematic illustration of a structure of a sensor 100 for detecting an analyte in an environment, in accordance with one embodiment of the invention. The sensor 100 may be a resonant inductor-capacitor-resistor (LCR) sensor. The analyte in the environment may be a volatile compound in the air.

Figure 1B:
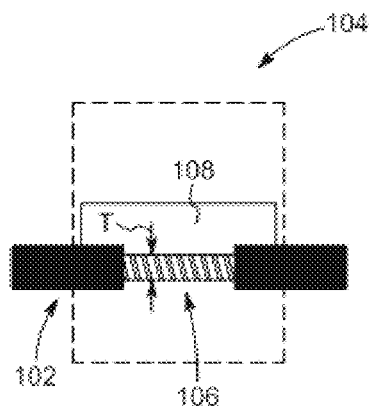
FIG. 1B is a zoomed in (side cross-sectional view) schematic representation of the sensor of FIG. 1A taken along the line I-I.

As shown in FIG. 1B, the sensor 100 comprises a sensor electrode 102 and a conducting element 106 operationally coupled to a discrete segment of the sensor electrode 102 and completes an electrical circuit of the sensor electrode 102. As further illustrated in FIG. 1B, the zoomed in (side cross-sectional view) schematic representation of the sensor of FIG. 1A taken along the line I-I, an activation material 108 is deposited in operational contact with, for example, adjacent to or on a surface of, the conducting element 106. The activation material 108 interacts with the analyte in the environment to produce an interaction product 107 (not shown), which further interacts with or exposes to the conducting element 106 and promotes or affects irreversible changes of at least one property of the conducting element 106. The irreversible changes of the conducting element 106 may be a physical change or a change in its chemical composition due to a chemical transformation of the conducting element 106 upon interacting with or being exposed to the interaction product 107.

The irreversible changes of at least one properties of the conducting element 106 may include changes of at least one of dielectric constant, conductivity, and a dielectric loss of the conducting element 106. In one example, when the conducting element 106 comprises a metal layer that is oxidized by the interaction product, the conductivity of the oxidized conducting element may be reduced. In another example, when the conducting element 106 comprises a metal salt layer that is reduced to a metal by the interaction product, an increase of the conductivity of the conducting element 106 may be achieved. Examples of the metal include but are not limited to silver, copper, and aluminum. Examples of the metal salts include but are not limited to copper acetate, zinc acetate, and silver nitrate.

The interaction of the analyte with the activation material 108 may be a physical or a chemical interaction, for example, catalytic reaction, aggregation-deaggregation, swelling, and dissolution.

Non-limiting examples of the activation material 108 includes solid acid catalysts, poly (styrene sulfonic acid), sulfonated zirconia, and others known in the art. The activation material 108 may be deposited by methods such as screen printing, ink-jet printing, flow coating, drop casting, and others known in the art.

To form the conducting element 106, materials such as silver, copper, and aluminum may be used. Non-limiting examples of methods for forming the conducting element include sputtering, vapor deposition, self-assembly, printing, and any other methods known in the art.

The conducting element 106 is operationally coupled to a discrete segment of the sensor electrode 102. As illustrated in FIGS. 1A and 1B, the discrete segment of the sensor electrode 102 is a segment of the sensor electrode 102 comprising a gap defined by a distance (D) formed between two free ends 102a and 102b of the discrete segment of the sensor electrode 102. The existence of the gap caused a complete loss of the resonance property of the electrical circuit of the sensor electrode 102 and led to a non-continuous structure of the sensor electrode 102. Next, each end of the conducting element 106 was coupled to the free ends 102a and 102b of the electrode 102, respectively. As a result, the conducting element 106 was operationally coupled to the discrete segment of the sensor electrode 102, and the electrical circuit and/or resonant circuit of the sensor electrode 102 was restored. The conducting element 106 may be coupled to the discrete segment of sensor electrode 102 via, for example, a lead wire, a dense or a porous film, screen-printed metal traces, inkjet-printed metal traces, etched metal traces, or others. The coupling may be achieved by methods such as soldering, using of conducting epoxy, clamping, or other known methods.

Parameters of the conducting element 106 includes, but not limited to, its dimension parameters, for example, a length (L), a width (W), and a thickness (T) of the conducting element 106. In FIG. 1A, the length (L) of the conducting element 106 is shown to be approximately the same as the distance (D) between the free ends (102a, 102b) of the sensor electrode 102 but it is to be appreciated that the length (L) of the conducting element may be shorter or longer than the distance (D) between the free ends of the sensor electrode in other embodiments.

In addition, it is to be appreciated that at least one of the thickness (T) or width (W) parameters of the conducting element 106 may be adjusted or configured to enable rapid irreversible change of at least one property of the conducting element 106 upon operational contact with the interaction product 107. In certain embodiments, at least one of the thickness (T) or width (W) parameters of the conducting element 106 may be significantly smaller in size compared to the length (L) of the conducting element 106, for example, 20-50,000 times smaller. This tunable and versatile sensor design allows the conducting element 106 to be easily tailored for selected sensing applications such that the irreversible change of the conducting element 106 may occur rapidly under the desirable sensing time frame for each sensing application.

The conducting element 106 may use same material or a material different than a material used in the sensor electrode 102, offering additional benefits for tuning the parameters of the conducting element 106 for selected sensing applications.

The conducting element 106 may be a single use or disposable unit and may be disposed of after each use.

The sensor 100 may further include a memory chip 109 coupled to the sensor electrode 102. The memory chip 109 may include manufacturing, user, calibration and/or other data stored thereon. The memory chip 109 is an integrated circuit device and includes radio frequency (RF) signal modulation circuitry fabricated using a complementary metal-oxide semiconductor (CMOS) process and a non-volatile memory. The RF signal modulation circuitry components include a diode rectifier, a power supply voltage control, a modulator, a demodulator, a clock generator, and other components.

Figure 2A:
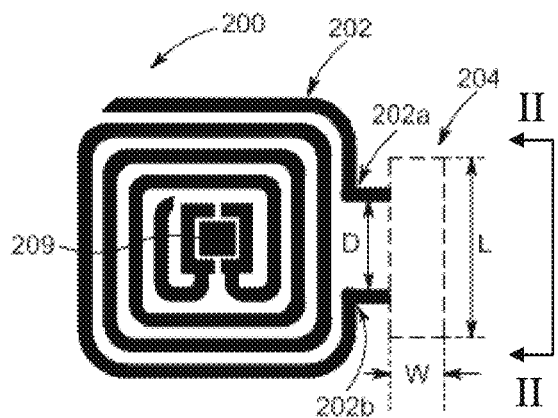
FIG. 2A is a schematic representation of a sensor according to an embodiment.
Figure 2B:
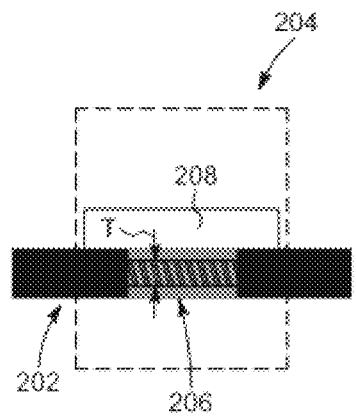
FIG. 2B is a zoomed in (side cross-sectional view) schematic representation of the sensor of FIG. 2A taken along the line II-II.

FIG. 2A is a schematic representation of a sensor 200 for detecting an analyte in an environment in accordance with another embodiment of the invention. In this design, an external conducting element 206 (as further illustrated in FIG. 2B) is operationally coupled to a discrete segment of a sensor electrode 202 to complete the electrical circuit of the sensor electrode 202. In one embodiment, the length (L) of the conducting element 206 is longer than the distance (D) between the free ends (202a, 202b) of the sensor electrode 202.

Figure 3C:
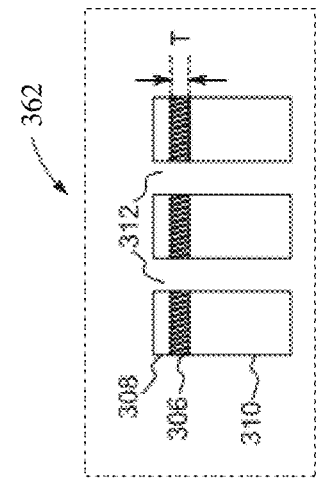
FIG. 3C is a zoomed in view of a schematic representation of a fluid passageway within the area 362 of FIG. 3B.
Figure 3B:
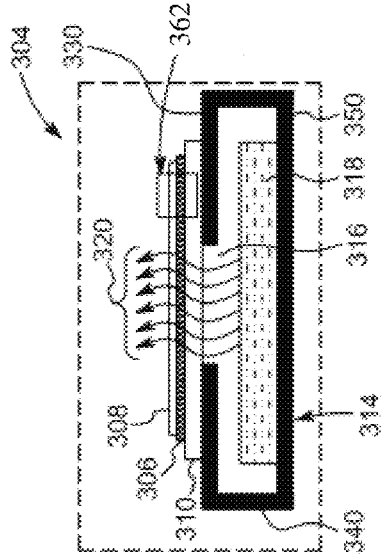
FIG. 3B is a zoomed in (side cross-sectional view) schematic representation of the sensor of FIG. 3A taken along the line III-III.
Figure 3A:
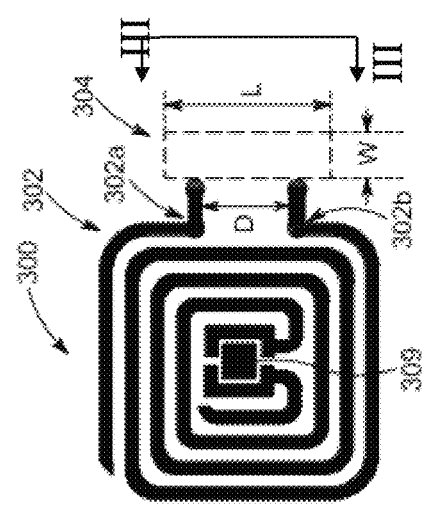
FIG. 3A is a schematic representation of a sensor according to an embodiment.

FIG. 3A is a schematic representation of a sensor 300 for detecting an analyte in an environment in accordance with yet another embodiment of the invention. The analyte may include a volatile compound in the environment and/or a non-volatile compound in a form of micro- or nano-particles dispersed in a gas phase.

Similar to the embodiment illustrated in FIGS. 1A and 1B, a conducting element 306 is operationally coupled to a discrete segment of a sensor electrode 302 to complete the electrical circuit of the sensor electrode 302. As further illustrated in FIG. 3B, the conducting element 306 may be optionally disposed on a porous substrate 310. An activation material 308 is deposited in operational contact with, for example, adjacent to or on a surface of, the conducting element 306. The activation material 308 may form a porous layer. Non-limiting examples of the activation material 308 include polystyrene sulfonic acid (PSS) and sulfonated zirconia.

As shown in FIG. 3B, a cartridge 314 comprising three sheet elements: a top element 330, a bottom element 350, and a spacer element 340 is also provided. The cartridge 314 may be fabricated from a transparent plastic, for instance, acrylic glass. All three elements may be bound together using a waterproof adhesive sealant, for example, a silicone adhesive sealant.

A solvent-absorbing pad 318 is enclosed between the top sheet element 330 and the bottom sheet element 350 and is surrounded by the spacer element 340. The top sheet element 330 comprises an opening or aperture 316. The bottom sheet element 350 has a small service hole 360 (not shown) for filling the cartridge 314 with a solvent (for example, water) prior to use and is subsequently sealed after the solvent-absorbing pad 318 has been moistened.

The solvent-absorbing pad 318 may be made of a sorbent material and impregnated with a solvent. Non-limiting examples of sorbent materials include polypropylene, high density polyethylene, polyester, polyvinyl chloride, and other materials that can be in a form of a mesh, yarn, fleece or other porous constructions. In one embodiment, the solvent-absorbing pad 318 is made from a glass microfiber porous filter, for example, a Whatman® Grade GF/B glass microfiber filter (GE Healthcare Bio-Sciences, Marlborough, Mass.).

The preferred solvent used by the solvent-absorbing pad 318 is water but other solvents such as alcohol, isopropanol, dimethylformamide, or others may be used.

As shown in FIG. 3C, together, the aperture 316 of the cartridge 314, the optional porous substrate 310, the conducting element 306, and the activation material 308 form a fluid passageway 312 for directing a fluid vapor 320 originating from the solvent-absorbing pad 318 to escape into the surrounding relatively dry environment through the fluid passageway 312. In addition, the porous substrate 310 may be disposed on top of the aperture 316 of the cartridge 314 and covers at least the aperture 316 to allow the fluid vapor 320 to escape into the surrounding environment through the fluid passageway 312.

The conducting element 306 may comprise metal which forms a sensing region. Non-limiting examples of metal include silver, copper, and aluminum. The conducting element 306 may be deposited in operational contact with the porous substrate 310 in a form of a line generated using a shadow mask such as a shadow nickel mask. Non-limiting examples of deposition methods include sputter deposition.

Non-limiting examples of the porous substrate 310 include polycarbonate track-etch (PCTE) membrane and nanoporous $Al_2O_3$ (aluminium oxide or alumina) membrane.

The conducting element 306 and/or the cartridge 314 may be a single use or disposable unit.

Figure 4A:
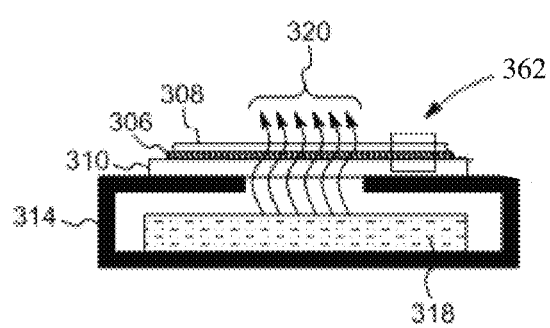
FIG. 4A is a partial schematic representation of the sensor as shown in FIG. 3A taken along the line III-III.
Figure 4B:
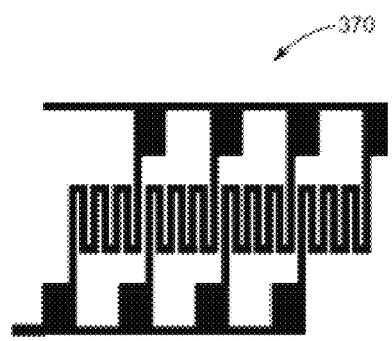
FIG. 4B is a zoomed in (top view) schematic representation of a meander array 370 within the area 362 of FIG. 4A.

As shown in FIGS. 4A and 4B, to increase the sensing area for improved sensor performance, the conducting element 306 of an embodiment shown in FIG. 4A may comprise a meander array 370 disposed between the porous substrate 310 and the activation material 308. The meander array 370 may include multiple meanders connected to each other in a pattern. A schematic drawing of such meander array 370 is shown in FIG. 4B.

Referring now to FIG. 3A, the conducting element 306 comprising the meander array 370 is operationally coupled to a discrete segment of the sensor electrode 302. The discrete segment of the sensor electrode 302 comprises a gap defined by a distance (D) formed between two free ends 302a and 302b of the discrete segment of the sensor electrode 302. The existence of the gap caused a complete loss of the resonance property of the circuit of the sensor electrode 302. Next, each end of the conducting element 306 was coupled to the free ends 302a and 302b of the electrode 302, respectively. As a result, the conducting element 306 was operationally coupled to the discrete segment of the sensor electrode 302, and the resonant circuit of the sensor electrode 302 was restored. The conducting element 306 may be coupled to the sensor electrode 302 via, for example, a lead wire, a dense or a porous film, screen-printed metal traces, inkjet-printed metal traces, etched metal traces, or others. The coupling may be achieved by methods such as soldering, using of conducting epoxy, clamping, or others.

Figure 5:
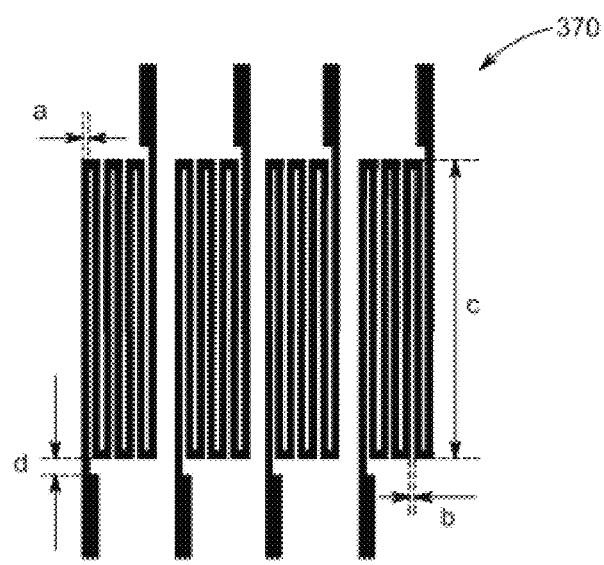
FIG. 5 is a schematic representation of a meander array according to an embodiment.

FIG. 5 shows a schematic illustration of a non-limiting example of the meander array 370 in accordance with the embodiment of FIG. 4B. In FIG. 5, the conducting element 306 comprising the meander array 370 in which four meanders are connected to each other in parallel. The conducting element 306 is then operationally coupled to the discrete segment of the sensor electrode 302, as described in FIG. 3A. Non-limiting examples of range for dimensions of the meander array 370 shown as (a)-(d) in FIG. 5 may be: (a) about 100-500 micrometers; (b) about 100-500 micrometers; (c) about 5-50 millimeters; and (d) about 0.5-10 millimeters. The meander array 370 may be fabricated by sputter deposition using a shadow mask with a pre-defined pattern. It is to be understood that the numbers of meanders used, the patterns and dimensions of each individual meander and/or the meander array disclosed herein are for illustration purpose only and are by no means limiting. Various modifications and alternative forms of meander array design are within the scope of this description.

Figure 6:
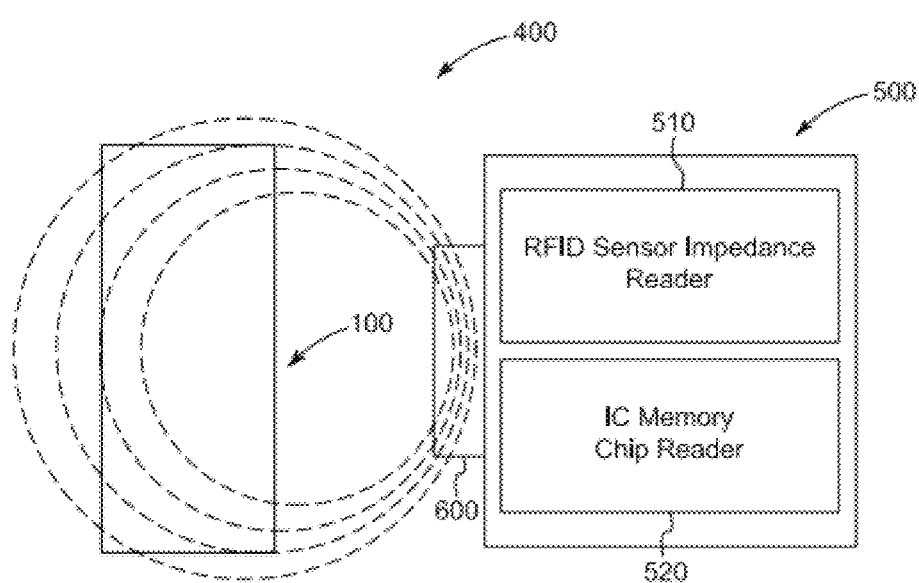
FIG. 6 is a schematic representation of a sensing system according to an embodiment.

FIG. 6 is a schematic drawing of a sensing system 400 in accordance with an embodiment. The sensing system 400 includes, for example, a sensor 100, a reader 500 communicatively coupled to the sensor 100 to obtain information from the sensor 100, and a communication unit 600 configured to provide an infrastructure for communication of the sensor 100 with the reader 500.

In certain embodiments, the sensor 100 may be interrogated or measured with the reader 500 or a device with incorporated readers that can obtain analog or digital information from the sensor 100. Non-limiting examples of devices with incorporated readers for reading the sensor response include a residential device, an industrial device, a home remote control, a home appliance, an industrial appliance, a device not connected to the network, a device connected to the network, a stationary device, a mobile device, a device for public security and protection, a medical device, an industrial safety device, a food safety device, a desktop device, a pocket-size device, and an embedded device.

The reader 500 may include a RFID sensor impedance reader 510, an integrated circuit memory chip reader 520, or both. Alternatively, the reader 500 may include only a RFID sensor impedance reader 510 without capability of reading the integrated circuit memory chip. The reader 500 may include other readers known in the art.

The sensing system 400 further includes a communication unit 600 configured to provide an infrastructure for communication of the sensor 100 with the reader 500. Non-limiting examples of communication modes for reading the sensor 100 include Wi-Fi™ Bluetooth™, Zigbee™, near field communication (NFC), inductive coupling, capacitive coupling, optical coupling, card emulation, tag reading, peer-to-peer, high-frequency (HF) communication, ultra-high-frequency (UHF) communication, ISO 15693, ISO 14443, ISO 18000-1, ISO 18000-2, ISO 18000-3, ISO 18000-4, ISO 18000-5, ISO 18000-6, ISO, 18000-6C, and ISO 18000-7.

Non-limiting examples of communication implementations include stand-off detection at distances ranging from about 1 meter to about 1000 kilometers, proximity detection at distances ranging from about 1 micrometer to about 1 meter, and non-galvanic contact detection in a "tapping" scenario for a short period of time or in a non-galvanic attachment scenario for a relatively long period of time.

EXAMPLES

Detection of Volatile Analytes in an Environment

In one embodiment according to FIG. 1A or FIG. 2A, a sensor 100 or 200 for detecting a triacetone triperoxide (TATP) analyte was developed. The sensor 100 or 200 includes a conducting element 106 or 206 in a form of a sputtered silver (Ag) film. Parameters such as length, thickness, and width of the conducting element 106 or 206 may be adjusted to optimize the sensor response.

Figure 7A:
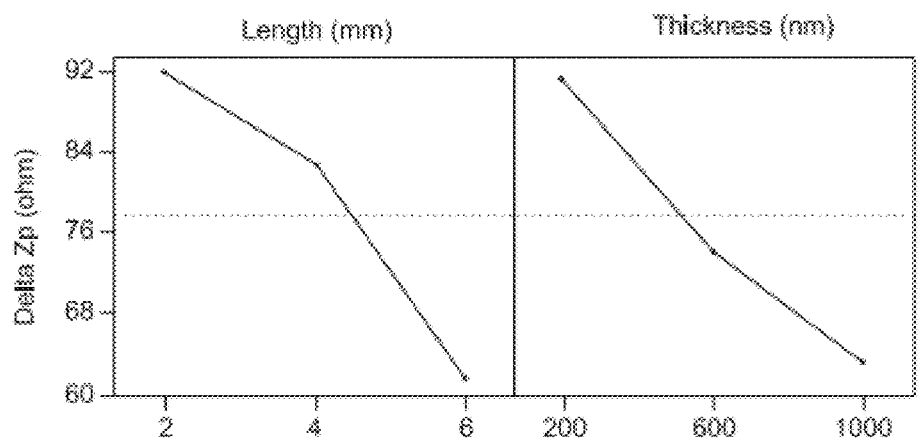
FIGS. 7A and 7B show the results of design of experiments (DOE) analysis of (7A) main effects plot and (7B) response surface plot of a sensor conducting element according to an embodiment.
Figure 7B:
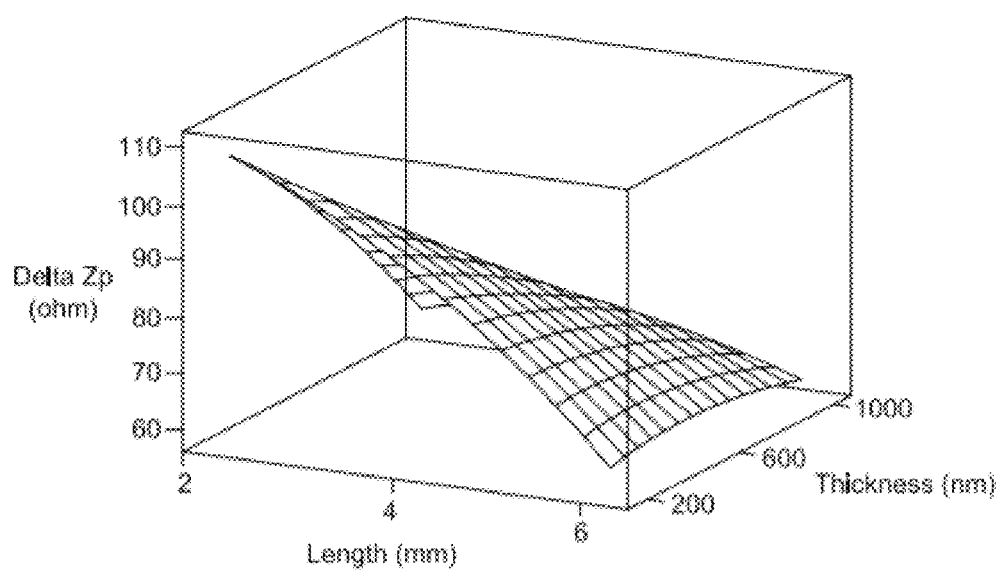

FIGS. 7A and 7B show the results of DOE analysis where the effect of parameters of a conducting element, for example, the conducting element 106 of FIG. 1A, on the sensor response were evaluated.

In all experiments, the sensor responses were measured in the presence of about 8 ppm of hydrogen peroxide ($H_2O_2$), which represents an interaction product between an analyte of 2 μg of TATP with an activation material comprising polystyrene sulfonic acid (PSS).

FIG. 7A represents the main effects plot of the response Delta Zp (ΔZp) as a function of the length and the thickness of a conducting element, for example, the conducting element 106 of FIG. 1A comprising sputtered silver (Ag) film. FIG. 7A suggests that a conducting element, such as the conducting element 106 of FIG. 1A, having a length shorter than 2 mm and thickness smaller than 200 nm gave larger sensing responses.

FIG. 7B represents the surface plot of the response Delta Zp (ΔZp) as a function of both the length and the thickness of a conducting element, for example, the conducting element 106 of FIG. 1A comprising sputtered silver (Ag) film. Thinner conducting element with shorter lengths showed higher sensing responses as shown in FIG. 7B.

Figure 8A:
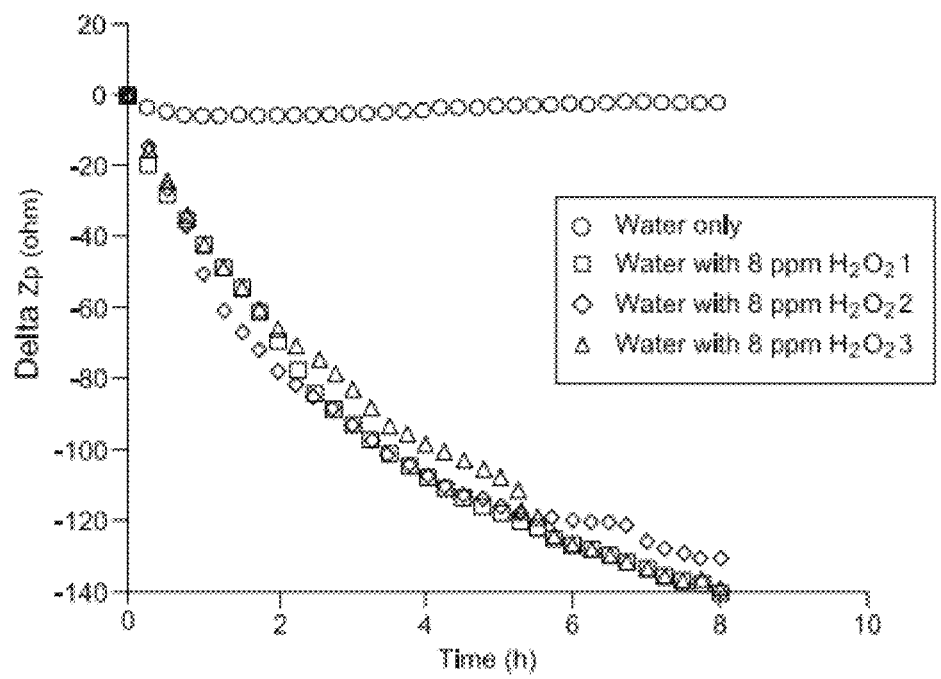
FIGS. 8A and 8B show responses (Delta Zp/$\Delta$Zp) of sensors with a sputtered silver (Ag) conducting element having 100 nm thickness and (8A) 1 mm length; and (8B) 2 mm length for water with 8 ppm $H_2O_2$ (8A); and water with 100 ppm $H_2O_2$ (8B), respectively, according to an embodiment.
Figure 8B:
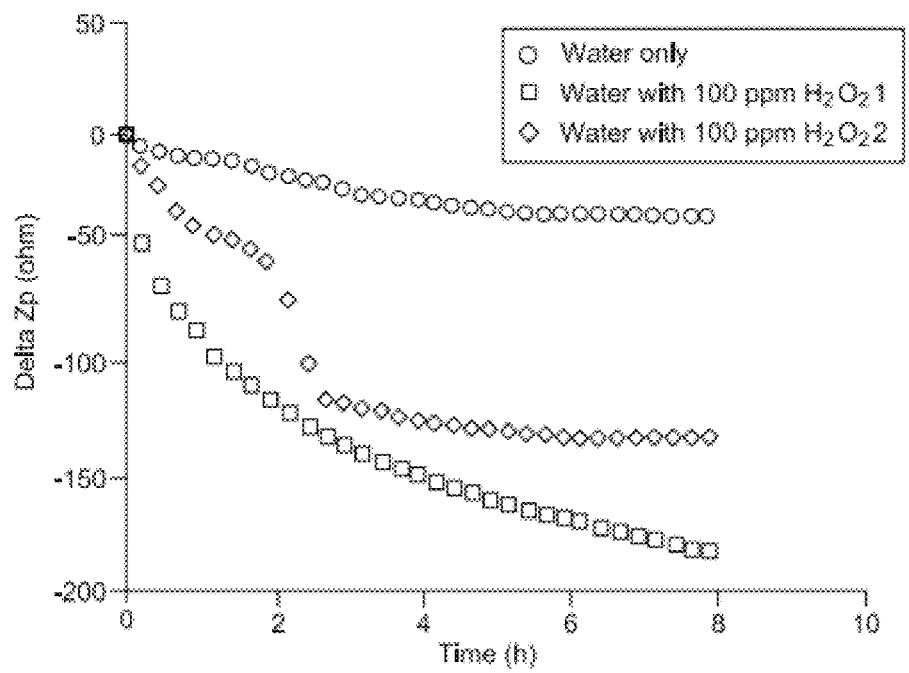

Next, the parameters of a conducting element, for example, the conducting element 106 of FIG. 1A were further optimization, as shown in FIGS. 8A and 8B. The sensor 100 used in FIGS. 8A and 8B include the conducting element 106 of FIG. 1A comprising sputtered silver film.

FIGS. 8A and 8B represent Delta Zp response (ΔZp) of a sensor, for example, the sensor 100 of FIG. 1A with the conducting element 106 of FIG. 1A with length of 2 mm and 1 mm, in FIGS. 8A and 8B, respectively.

The thickness of the conducting element 106 of FIG. 1A was the same (100 nm) for the sensors tested in both FIGS. 8A and 8B. To evaluate the interference effect, a sensor response curve was generated with water instead of 8 ppm of $H_2O_2$ under the otherwise identical testing conditions. Both sensors 100 of FIG. 1A have similar sensing response profiles when tested in FIGS. 8A and 8B. However, the sensor tested in FIG. 8A showed lower response to the interference (water) compared to the sensor tested in FIG. 8B. In addition, the sensor tested in FIG. 8A enables detection of $H_2O_2$ with higher sensitivity and more robust reproducibility (for example, ΔZp of about 140 ohm and standard deviation of the replicate measurements (n=3) is about 4.75 ohm at 8 hours in FIG. 8A). Therefore, the sensor 100 having the conducting element 106 of FIG. 1A with the 100 nm thickness and 2 mm length demonstrated better performance and was used in subsequent tests.

Figure 9:
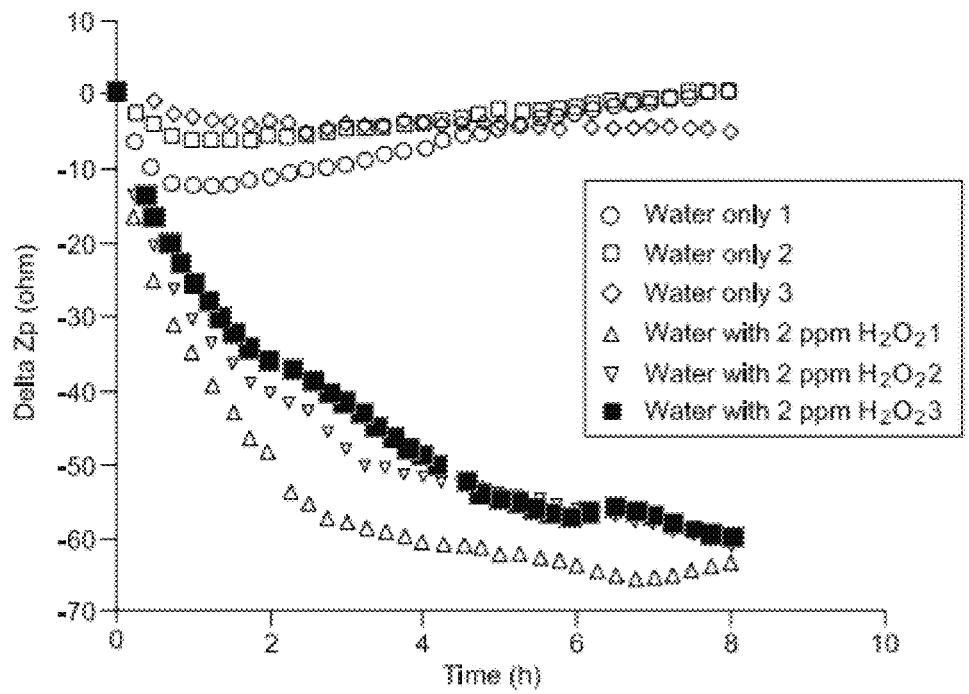
FIG. 9 shows Delta Zp response of a sensor for water with 2 ppm $H_2O_2$, according to an embodiment.

In FIG. 9, a conducting element, for example, the conducting element 106 of FIG. 1A with 100 nm thickness and 2 mm length was further tested in the presence of 2 ppm $H_2O_2$, which represents an interaction product between 500 ng of TATP analyte and an activation material comprising PSS.

To evaluate the interference effect, sensor response curves were generated with water instead of 2 ppm of $H_2O_2$ under the otherwise identical testing conditions. As shown in FIG. 9, significantly larger $\Delta Zp$ response was achieved in the presence of 2 ppm $H_2O_2$ compared to water. This demonstrated that the sensor 100 comprising the conducting element 106 of FIG. 1A with a 100 nm thickness and a 2 mm length is sufficient to achieve the desirable high analyte selectively and negligible response to interferences such as water.

Figure 10:
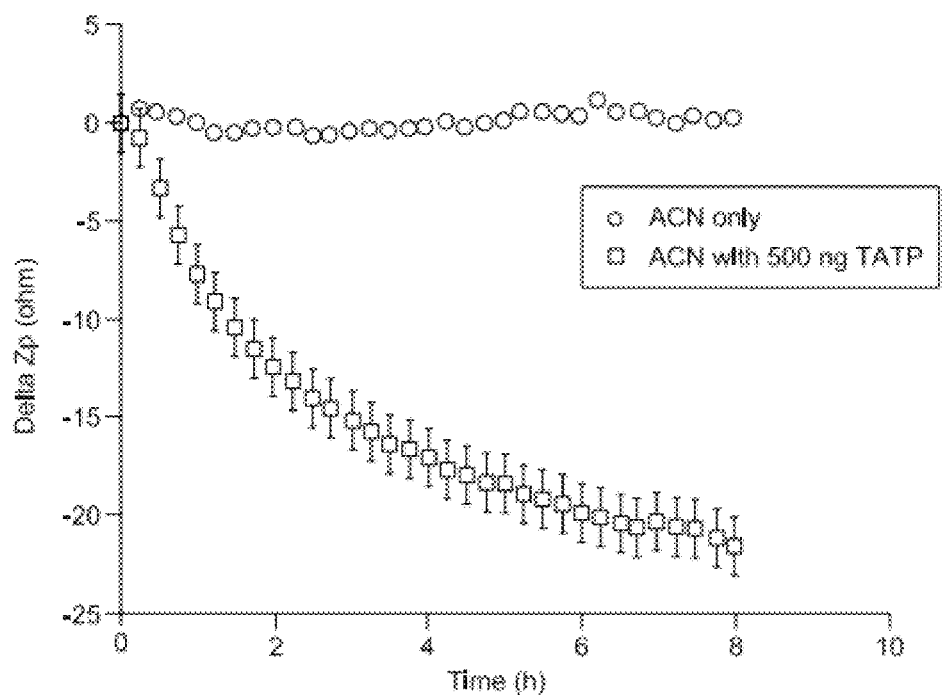
FIG. 10 shows $\Delta$Zp response of a sensor having silver as conducting element and polystyrene sulfonic acid (PSS) as activation material for 500 ng of TATP analyte, according to an embodiment.

In FIG. 10, a sensor, for example, the sensor 100 including a conducting element 106 of FIG. 1A in a form of a sputtered silver (Ag) film and an activation material comprising polystyrene sulfonic acid (PSS) was used. 500 ng of TATP was used as analyte. To test the interference effect, a sensor response curve was generated with acetonitrile (ACN) replacing an analyte of 500 ng of TATP under otherwise identical testing conditions. Interaction of the analyte (500 ng of TATP) with PSS forms an interaction product of hydrogen peroxide ($H_2O_2$) having a concentration of about 2 ppm. The interaction product ($H_2O_2$) irreversibly oxidized the silver film of the conducting element 106 of FIG. 1A. This irreversible change of the conducting element 106 of FIG. 1A includes one or more changes in the property of the conducting element 106, for example, the impedance property of the conducting element 106 of FIG. 1A was changed, which further induced an irreversible sensor response represented by $\Delta Zp$. In contrast, no interaction product was formed between the interference (acetonitrile in this case) and the activation materials, and no irreversible changes occurred to the conducting element 106 of FIG. 1A, thus no detectable irreversible sensor response was present.

As shown in FIG. 10, significantly larger sensor response ($\Delta Zp$) was achieved in the presence of 500 ng of TATP analyte (with replicate measurements n=3) compared to acetonitrile. This demonstrated that the sensor 100 of FIG. 1A is sufficient to achieve a high analyte selectivity and low response to interferences (for example, acetonitrile) in an environment.

Detection of Non-Volatile Analytes in an Environment

In one embodiment according to FIGS. 3A, 3B and 3C, a sensor 300 was developed to enable detection of non-volatile analytes such as particles deposited on the sensor surface under a relatively dry environment. The sensor 300 includes a porous substrate 310, a conducting element 306 comprising a meander array 370, and a layer of porous activation material 308.

The porous substrate 310 is in operational contact with the conducting element 306 and a fluid vapor 320. The operational contact may be achieved by direct contact or through a gap that nevertheless provides a chemical or physical contact.

In certain embodiments, the porous substrate 310 allows a fluid vapor 320 (for example, water) to interact with non-volatile analytes (for example, dissolve oxidizer particles) deposited on the meander array 370 to enable sensing of the non-volatile analytes in a relatively dry environment.

A non-limiting example of material for the porous substrate 310 includes polycarbonate track-etch (PCTE) membrane filter (Sterlitech Corporation, Kent, Wash.). A conducting element 306 comprising a silver line of 1 mm of length (L) and 100 nm of thickness (T) was deposited in operational contact with the porous substrate 310 by sputter deposition method through a shadow nickel mask. Lead wires were soldered to the ends of the conducting element 306 and then connected to a discrete segment of the sensor electrode 302. For example, one of the metal turns of the sensor electrode 302 was cut to expose a discrete segment of the sensor electrode 302, which led to a complete loss of the resonance property of the electrical circuit of the sensor electrode 302. Then the resonant circuit continuity was restored by connecting the conducting element 306 with the lead wires to the two free ends of the discrete segment of the sensor electrode 302. Because the conducting element 306 shows sizable electric resistance it affects the sensor electrode's resonance property, causing a shift of the resonance peak to lower frequencies and a decrease in the peak amplitude (Zp) and the peak Q factor. The irreversible change of the conducting element 306 (for example, oxidation of the conducting element 306) caused a desirable change of at least one of its properties (for example, increase in its resistance), causing a gradual Zp decrease to the point when the sensor electrode 302 stopped to resonate.

One way to increase the sensing area was to build a conducting element 306 comprising a meander array 370 where multiple meanders are connected to each other in parallel. A schematic example of such design is shown in FIG. 5, in which four meanders are connected in parallel. The total sensing area of this structure is about 3 $cm^2$.

Figure 11:
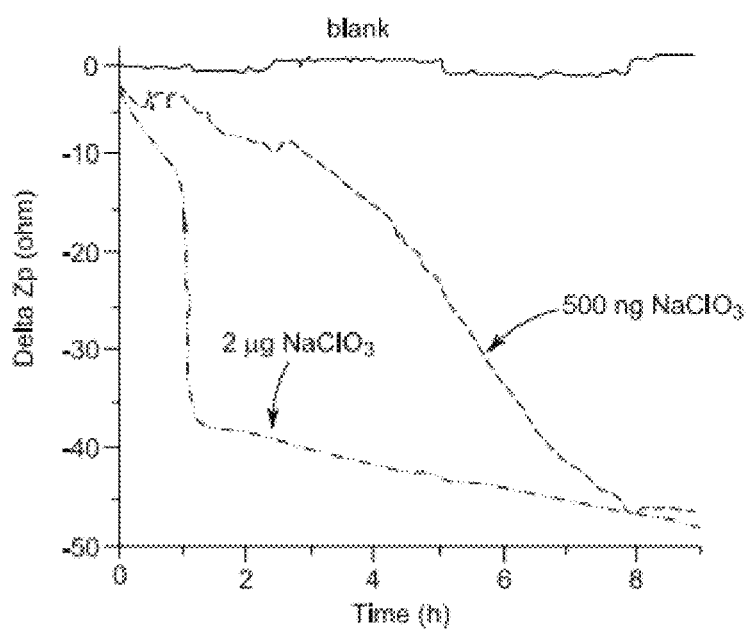
FIG. 11 shows sensor response to non-volatile $NaClO_3$ particles using a sensor according to an embodiment of FIG. 3A.

FIG. 11 shows an example of sensor response ($\Delta Zp$) to non-volatile particles ($NaClO_3$ particles), using a sensor 300 in accordance with an embodiment of FIG. 3A. The sensor 300 of FIG. 3A comprises the conducting element 306 of FIG. 4A having a thickness of about 100 nm. About 0.125% PSS was used as an activation material. A general working range of PSS may be from about 0.05% to about 0.5%. FIG. 8 shows that as low as 500 ng of $NaClO_3$ particles can be detected using the sensor 300 in accordance with an embodiment of FIG. 3A.

Figure 12:
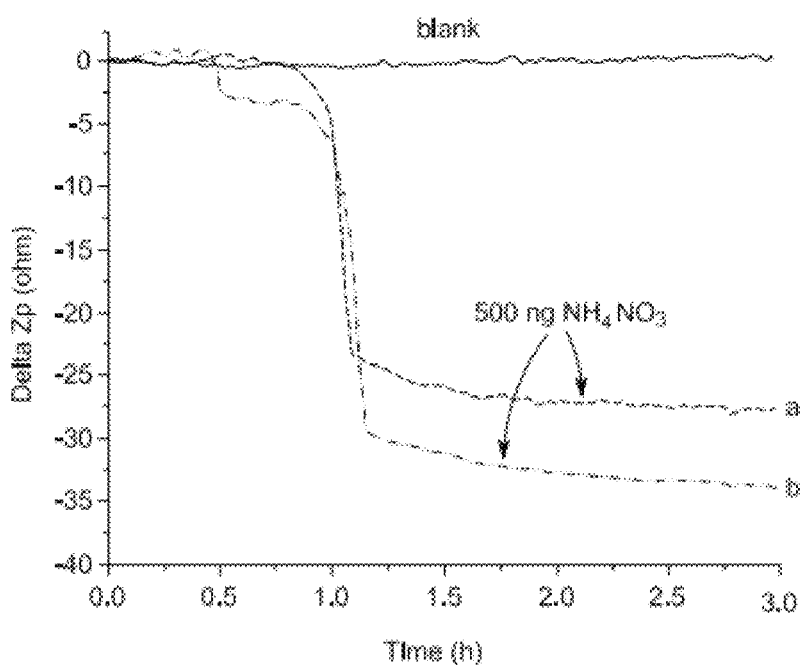
FIG. 12 shows sensor response to non-volatile $NH_4NO_3$ particles using a sensor according to an embodiment of FIG. 3A.

FIG. 12 shows an example of sensor response ($\Delta Zp$) to non-volatile $NH_4NO_3$ particles, using a sensor 300 in accordance with an embodiment of FIG. 3A. Curves (a) and (b) in FIG. 12 represent duplicated measurements. The sensor 300 of FIG. 3A comprises a conducting element 306 of FIG. 4A. The conducting element 306 of FIG. 4A further comprises a Copper-Silver (Cu—Ag) alloy containing Cu (about 100 nm thickness) and Ag (about 5 nm thickness). The weight ratio of Cu and Ag can be adjusted. The use of the Cu/Ag alloy at different ratios of Cu and Ag further provides potential tuning abilities of the conducting element 306 of FIG. 4A. Different combinations of activation materials and analytes may promote or affect different irreversible change of the conducting element comprises a tunable Cu—Ag alloy.

Figure 13A:
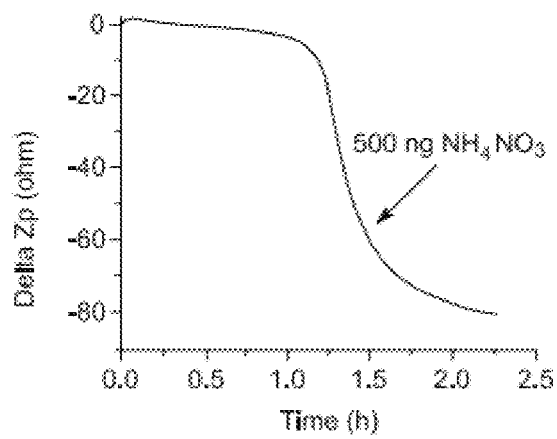
FIGS. 13A and 13B show sensor response to non-volatile (13A) $NH_4NO_3$ and (13B) $NaClO_3$ particles with a Copper-silver (Cu—Ag) alloy as the conducting element according to an embodiment.
Figure 13B:
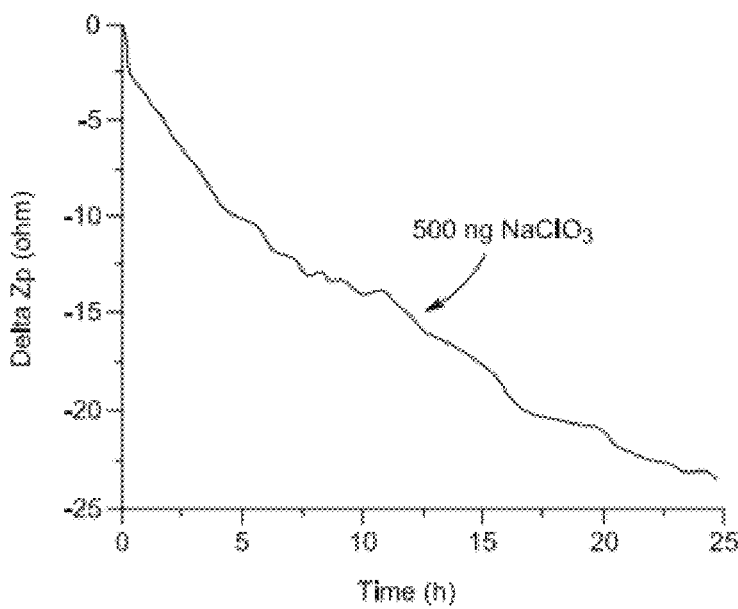

FIGS. 13A and 13B show examples of responses of a sensor (Delta Zp), for example, the sensor 300 of FIG. 3A, to non-volatile (13A) $NH_4NO_3$ and (13B) $NaClO_3$ particles. The sensor 300 of FIG. 3A comprises a conducting element 306 of FIG. 4A. The conducting element 306 of FIG. 4A comprises a Cu—Ag alloy and has about 100 nm in thickness and about 1 mm in length. FIG. 13A illustrates that upon exposure of the Cu—Ag alloy to 500 ng of $NH_4NO_3$ analyte the sensor response (ΔZp) had a decrease with an S-shape profile where the initial response had a small slope, followed by the relatively higher slope of the response and followed further by the relatively smaller slope. FIG. 13B illustrates that upon exposure of the Cu—Ag alloy to 500 ng of $NaClO_3$ the sensor response (ΔZp) had an exponential decrease of the ΔZp signal.

FIG. 13A shows that upon exposure of the Cu—Ag alloy to 500 ng of $NH_4NO_3$ analyte, the sensor response (ΔZp) had a decrease with an S-shape profile where the initial response had a small slope, followed by the relatively higher slope of the response and followed further by the relatively smaller slope. The reaction was substantially completed under three hours from the beginning of the reaction.

FIG. 13B shows that upon exposure of the Cu—Ag alloy to 500 ng of $NaClO_3$ the sensor response (ΔZp) had an exponential decrease of the ΔZp signal. The reaction was substantially continuing after 25 hours from the beginning of the reaction.

Figure 14:
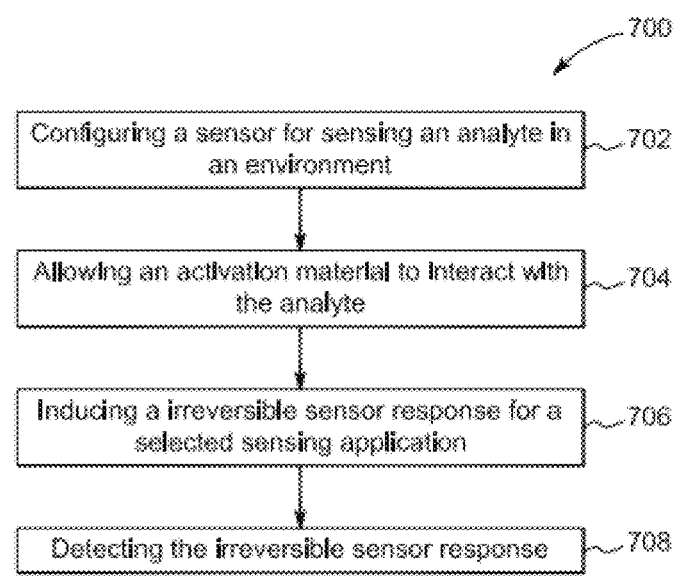
FIG. 14 is a flow diagram of a method according to an embodiment.

FIG. 14 is a flow diagram of a method 700 for sensing an analyte in an environment. The method 700 comprises the steps of: configuring a sensor for sensing the analyte in the environment (702), the sensor comprising: a sensor electrode; a conducting element operationally coupled to a discrete segment of the sensor electrode; and an activation material in operational contact with the conducting element and configured to induce an irreversible sensor response for a selected sensing application; allowing the activation material to interact with the analyte (704); inducing the irreversible sensor response for the selected sensing application (706); and detecting the irreversible sensor response (708).

In FIG. 14, various operations are depicted in the blocks to illustrate the functions that may be performed in the method. It should be understood that certain blocks may be deleted from the illustrated method or augmented by additional blocks with added functionality without departing from the spirit and scope of the subject matter described herein.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A sensor for sensing an analyte in an environment, the sensor comprising:
    a sensor electrode, wherein the sensor electrode comprises a non-continuous structure formed of a first material;
    a conducting element comprising a second material that is conductively coupled to the sensor electrode to complete an electrical circuit of the sensor electrode, wherein the first material and the second material are different; and
    an activation material in operational contact with the conducting element and configured to induce an irreversible sensor response for a selected sensing application.

2. The sensor of claim 1, wherein the conducting element is configured to complete a resonant circuit of the sensor electrode.

3. The sensor of claim 1, wherein the first material of the conducting element comprises a metal.

4. The sensor of claim 1, wherein the conducting element comprises a meander array that comprises a plurality of meanders coupled to one another in parallel.

5. The sensor of claim 1, wherein the conducting element is single use or disposable.

6. The sensor of claim 1, wherein the activation material is configured to interact with the analyte in the environment to affect a change of at least one property of the conducting element.

7. The sensor of claim 6, wherein the change of the at least one property of the conducting element comprises changes of at least one of dielectric constant, conductivity, and a dielectric loss of the conducting element.

8. The sensor of claim 6, wherein the change of the at least one property of the conducting element is a result of a chemical transformation of the conducting element.

9. The sensor of claim 6, wherein the change of the at least one property of the conducting element is irreversible.

10. The sensor of claim 1, wherein the analyte comprises a volatile compound.

11. The sensor of claim 1, wherein the analyte comprises a non-volatile compound.

12. The sensor of claim 1, further comprising a porous substrate in operational contact with the conducting element.

13. The sensor of claim 12, wherein the conducting element comprises a meander array.

14. The sensor of claim 12, wherein the activation material is porous.

15. The sensor of claim 12, wherein the analyte comprises a non-volatile compound.

16. The sensor of claim 12, further comprising a cartridge having an aperture, wherein the porous substrate is in operational contact with the cartridge and covers at least the aperture of the cartridge.

17. The sensor of claim 16, wherein the aperture of the cartridge, the porous substrate, and the conducting element define a fluid passageway for directing a flow of a fluid vapor formed inside the cartridge.

18. The sensor of claim 16, further comprises a solvent-absorbing pad enclosed inside the cartridge.

19. The sensor of claim 16, wherein at least one of the conducting element and the cartridge is single use or disposable.

20. The sensor of claim 1, wherein the non-continuous structure of the sensor electrode comprises a first portion and a second portion, and wherein the conducting element is coupled between the first portion and the second portion of the sensor electrode.

21. The sensor of claim 1, wherein the conducting element is replaceable by a replacement conducting element having the first material, the second material, or a third material, and wherein the first material, the second material, and the third material are different.

22. A method for sensing an analyte in an environment, the method comprising:
    configuring a sensor for sensing the analyte in the environment, the sensor comprising:
        a sensor electrode, wherein the sensor electrode comprises a non-continuous structure formed of a first material;
        a conducting element comprising a second material that is conductively coupled to the sensor electrode to complete an electrical circuit of the sensor electrode, wherein the first material and the second material are different; and an activation material in operational contact with the conducting element and configured to induce an irreversible sensor response for a selected sensing application;

allowing the activation material to interact with the analyte;

inducing the irreversible sensor response for the selected sensing application; and detecting the irreversible sensor response.

23. The method of claim 22, further comprising affecting an irreversible change of at least one property of the conducting element.

24. The method of claim 22, further comprising monitoring the irreversible sensor response for the selected sensing application.

25. The method of claim 22, wherein the sensing application comprises at least one of biopharmaceutical products monitoring, food or beverages monitoring, industrial monitoring of chemical or physical hazards, residential home monitoring, homeland security monitoring, personal care monitoring, occupational exposure monitoring, air monitoring, or water monitoring.

26. A system for sensing an analyte in an environment, the system comprising:

a sensor comprising:

a sensor electrode, wherein the sensor electrode comprises a non-continuous structure formed of a first material;

a conducting element comprising a second material that is conductively coupled to the sensor electrode to complete an electrical circuit of the sensor electrode, wherein the first material and the second material are different; and an activation material in operational contact with the conducting element and configured to induce an irreversible sensor response for a selected sensing application;

a reader communicatively coupled to the sensor to obtain information from the sensor; and a communication unit configured to provide an infrastructure for communication of the sensor with the reader.

27. The system of claim 26, wherein the reader is a RFID sensor impedance reader or an integrated circuit memory chip reader.

* * * * *